(12) United States Patent
Kanevsky et al.

(10) Patent No.: US 6,236,968 B1
(45) Date of Patent: May 22, 2001

(54) SLEEP PREVENTION DIALOG BASED CAR SYSTEM

(75) Inventors: Dimitri Kanevsky, Ossining; Wlodek Wlodzimierz Zadrozny, Tarrytown, both of NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 09/078,807

(22) Filed: May 14, 1998

(51) Int. Cl.[7] .................................................. G10L 21/00
(52) U.S. Cl. ............................................ 704/275; 704/270
(58) Field of Search .................................... 704/270, 274, 704/275, 272, 257, 251, 258

(56) References Cited

U.S. PATENT DOCUMENTS

| | | | |
|---|---|---|---|
| 3,707,710 | 12/1972 | Adler et al. ........................ | 340/272 |
| 5,101,926 | 4/1992 | Berman et al. ..................... | 180/272 |
| 5,559,927 | 9/1996 | Clynes ............................... | 395/267 |
| 5,577,165 | * 11/1996 | Takebayashi et al. .............. | 704/275 |
| 5,649,060 | 7/1997 | Ellozy et al. . | |
| 5,684,455 | 11/1997 | Williams et al. .................... | 340/439 |
| 5,694,116 | * 12/1997 | Kojima ............................... | 340/576 |
| 5,745,031 | 4/1998 | Yamamoto .......................... | 340/439 |
| 5,774,860 | * 6/1998 | Bayya et al. ........................ | 704/275 |
| 5,786,765 | 7/1998 | Kumakura et al. ................. | 340/576 |
| 5,809,269 | * 9/1998 | Favot et al. ......................... | 712/200 |
| 5,915,238 | * 6/1999 | Tjaden ................................. | 704/260 |
| 5,952,928 | 9/1999 | Washington et al. ............... | 340/575 |
| 5,983,189 | * 11/1999 | Lee ..................................... | 704/275 |
| 5,990,795 | 11/1999 | Miller ................................. | 340/576 |
| 6,009,355 | * 12/1999 | Obradovich et al. ............... | 707/1 |
| 6,048,324 | 4/2000 | Socci et al. ......................... | 600/595 |

FOREIGN PATENT DOCUMENTS

| | | | |
|---|---|---|---|
| 1234345 | 11/1999 | (CN) ............................. | B60K/28/06 |
| 2111134 | 5/1998 | (RU) ............................. | B60K/28/06 |

OTHER PUBLICATIONS

"The Design and Implementation of the TRAINS–96 System: A Prototype Mixed–Initiative Planning Assistant", G. Ferguson et al., The University of Rochester, Computer Science Department, TRAINS Technical Note 96–5, Oct. 1996.

C. Lee et al, Automatic Speech and Speaker Recognition, An Overview of Automatic Speech Recognition, pp. 1–5, 1996.

F. Jelinek et al, Decision Tree Parsing using a Hidden Derivation Model, IBM Research, T.J. Watson Research Center, Yorktown Heights, N.Y. 10598, 1994.

G. Gazdar, et al, Natural Language Processing in POP–11, An Introduction to Computational Linguistics, Addison–Wesley Publishing Co., pp 21–27, 244–249, 356–361, 1989.

(List continued on next page.)

Primary Examiner—Richemond Dorvil
Assistant Examiner—Angela Armstrong
(74) Attorney, Agent, or Firm—Sughrue, Mion, Zinn, Macpeak & Seas, PLLC

(57) ABSTRACT

An automatic dialog system capable of keeping a drive awake while driving during a long trip or one that extends into the late evening. The system carries on a conversation with the driver on various topics utilizing a natural dialog car system. The system includes an automatic speech recognition module, a speech generation module which includes speech synthesis or recorded speech, and possibly dynamically combined speech synthesizer and recorded speech, and a natural language processing module. The natural dialog car system analyzes a driver's answer and the contents of the answer together with his voice patterns to determine if he is alert while driving. The system warns the driver or changes the topic of conversation if the system determines that the driver is about to fall asleep. The system may also detect whether a driver is effected by alcohol or drugs.

16 Claims, 4 Drawing Sheets

OTHER PUBLICATIONS

L.R. Bahl et al, A Tree–Based Statistical Language Model for Natural Language Speech Recognition, IEEE Transaction on Acoustics, Speeck and Signal Processing, vol. 37, No. 7, Jul. 1989, pp 1001–1008.

W.G. Lehnert, BORIS—An Experiment in In–Depth Understanding of Narratives, Artificial Intelligence, pp 15–63, 1983.

* cited by examiner

SLEEP PREVENTION DIALOG BASED CAR SYSTEM

BACKGROUND OF THE INVENTION

The present invention is directed in general to an automatic dialog car system. More particularly, the invention is directed to an automatic dialog car system designed to prevent a driver from falling asleep during long trips or trips that extend into the evening.

A leading cause of traffic accidents is by drivers who fall asleep at the wheel. There exist various devices designed to prevent drivers from falling asleep. For example, one conventional device includes a miniature system installed in a driver's hat, to measure the slope of the driver's head. If the slope of the driver's head exceeds a predetermined threshold, a loud audible signal is generated to awaken the driver. The problem with such a prevention system is that the driver can lose control of the car several moments before his head changes positions. That is, a driver may fall asleep before his head drops beyond the threshold that triggers the audible signal. Various other methods have been tried, for example, the use of stimulation drinks (e.g., coffee and tea) and tablets for preventing drivers from sleeping during such situations. However, all such methods have not been successful.

It is well known that to keep the driver awake while driving, he should talk with someone in the car (or over a car telephone). However, it is obvious that such options are not always available for those times when a driver is driving alone in the car or a car telephone is not accessible.

SUMMARY OF THE INVENTION

Accordingly, in view of the above and other problems with the conventional art, it is an object of the present invention to provide an automatic dialog system that is capable of keeping a driver awake during long or evening trips. The system can carry on a conversation with a driver on any one of various topics with the help of a natural dialog car system. In such a system, the driver is obliged to participate in the conversation with the dialog car system. The natural dialog car system often includes humorous content for combating fatigue in the driver.

It is a further object of the present invention to provide a natural dialog car system including a natural language processing module that can understand the content of answers or questions uttered by a driver, and produce meaningful responses.

It is a further object of the present invention to provide a natural dialog car system for interpreting a driver's answers and producing machine responses.

An even further object of the present invention is to provide a natural dialog car system that understands content of tapes, books and radio programs, and extracts and reproduces appropriate phrases from those materials while it is talking with a driver. For example, a system can find out if someone is singing on a channel of a radio station. The system will state "And now you will hear a wonderful song!" or detect that there is news and state "Do you know what happened now—hear the following—and play some news." The system also includes a recognition system to detect who is speaking over the radio and alert the driver if the person speaking is one the driver wishes to hear.

According to yet a further object of the present invention, there is provided a natural dialog car system directed to human factor engineering, for example, people using different strategies to talk. For instance, short vs. elaborate responses. In this manner, the individual is guided to talk in a certain way so as to make the system work (e.g., "sorry I didn't get it, could you say it briefly"). Here, the system defines a narrow topic of the user reply (answer or question) via an association of classes of relevant words via decision trees. The system builds a reply sentence asking what are most probable word sequences that could follow the users' reply.

According to yet a further object of the present invention, there is provided a natural dialog car system including a conversation planner for keeping the driver alert. An analyzer of the driver's answers and content of the answers and his voice patterns are judged to determine the alertness of the driver while he is driving. This module contains a set of prototypes for different voice patterns corresponding to different levels of a driver's alertness. The system analyzes the quality of the driver's answers, and detects a time that is needed for the driver to answer. The system matches the output parameters (response time and quality of answers, etc.) with a table and determines whether the driver conditions from this and the other set of parameters. The system alerts a driver or changes a topic of conversation and/or sounds an alarm if it finds that he is tired or about to fall asleep. The system may detect whether a driver is effected by drug or alcohol in this manner as well.

DETAILED DESCRIPTION OF THE INVENTION

Figure 1:
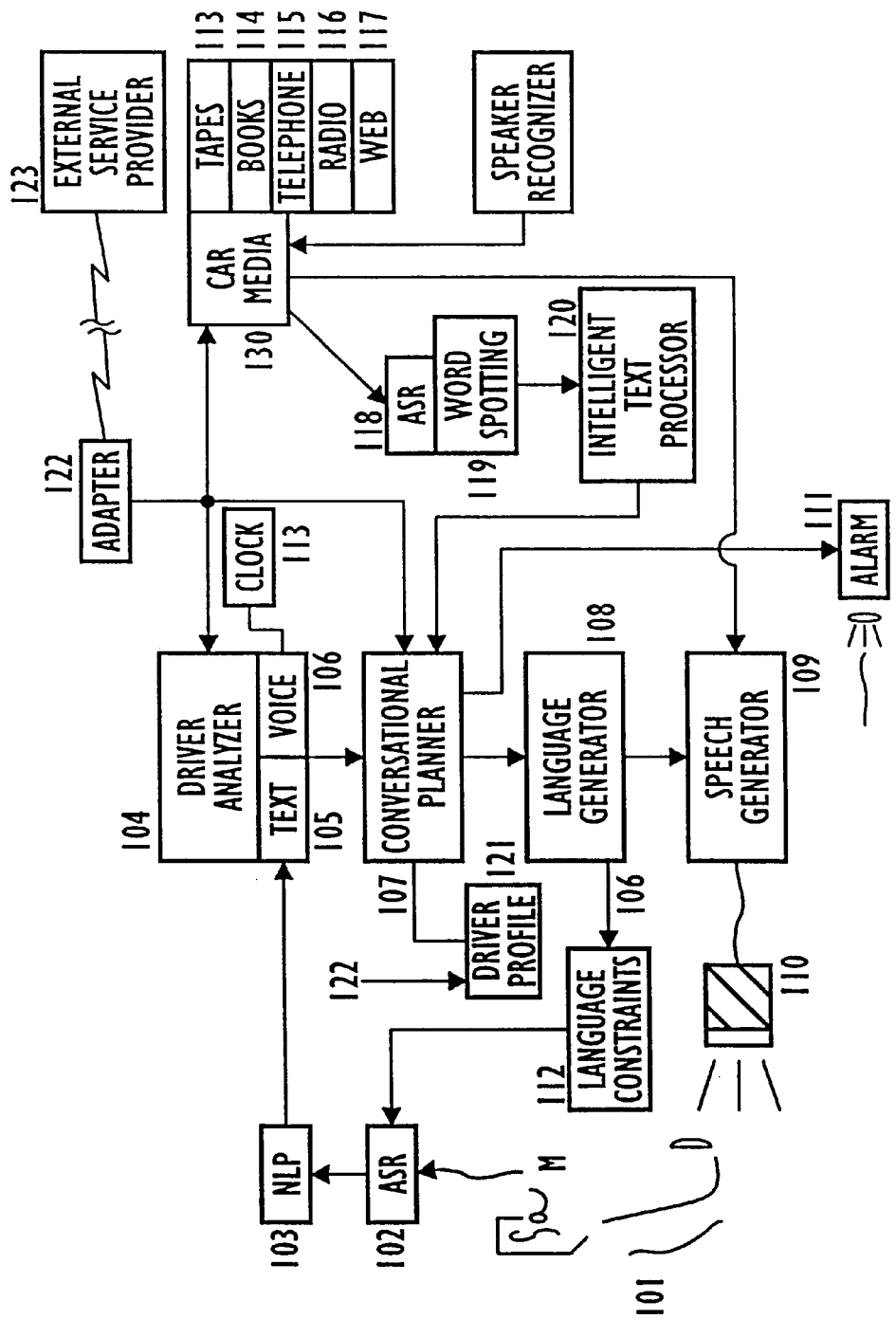
FIG. 1 is a block diagram of a an automatic car dialog system according to a preferred embodiment of the present invention.

Referring to FIG. 1, voice input from a driver 101 is applied to a first automatic speech recognition unit ("ASR") 102 and to a voice unit module 106 of a driver analyzer module 104 where the characteristics of the driver's voice are measured. The module 104 determines as to whether the driver is alert. A microphone M may be placed near the driver for the driver to speak in to reduce the effect of car noise during the recognition and decoding of speech by the ASR module 102.

The ASR module 102 is known in the art and reference is made in particular to Chin-hui Lee, Frank K. Soong, Kuldip K. Paliwal, "Automatic Speech and Speaker Recognition," Kluwer Academic Publisher, Boston 1996), which is incorporated herein by reference. The ASR module 102 may be one that is trained for the particular speaker or speaker independent. The ASR module 102 decodes the driver's speech under dynamic language constrains 112, and outputs a decoded signal to a natural language processor ("NLP") 103. These dynamic language constraints restrict the ASR module process to a predefined topic of conversation, which is defined by a language generator module 108. The module 108 produces machine responses to a driver and in this way defines the context of a driver's reply. This topic can be represented as a set of words that are associated to words generated by the language generator module 108. The associated topic words restrict the decoding of the ASR module 102 to a vocabulary that is composed of these topic related words and other common words. This procedure of decoding under dynamic constrains is similar to what is described in U.S. Pat. No. 5,649,060 to Ellozy et al., "Automatic Indexing and Aligning of audio and Text Speech Recognition." This patent is incorporated herein by reference.

A second ASR module 118 operates with a voice car media 130. The second ASR module 118 decodes, for example, tapes 113, audio books 114, radio programs 116, phone mails 115 and voice content of web sites 117, as well as other audio equipment such as CD player units or DVD player units. The decoding output of the ASR module 118 is analyzed by an intelligent text processor 120 that outputs data to a conversational planner 107. The system builds reply sentences relating to queries of words to the topic under discussion using different techniques known in the art such as: G. Lehnert et al. "BORIS—An Experiment In-Depth Understanding of Narratives" Artificial Intelligence Journal 20(1), January 1983, which is incorporated herein by reference, and G. Ferguson et al., "The Design and Implementation of the TRAINS-96 System: A Prototype Mixed-initiative Planning Assistant" TRAINS Technical Note 96-5. The University of Rochester, Computer Science Department, October 1996, which is also incorporated herein by reference.

The system may also include a word spotting module 119 to detect specific words in the car media 130. The specific words are used as spots for speech segments to be played to a driver during the conversation within the car.

Based on the data received from the intelligent text processor 120 and from the driver analyzer module 104, a conversational planner 107 decides whether voice information from the car media 130 should be applied to a speech generator 109 to be played for the driver as part of a response to the present dialog.

The NLP module 103, which is described in more detail below with respect to FIG. 2, processes the decoded signal of textual data from the ASR module 102. The NLP module 103 identifies semantic, pragmatic and syntactic content of the message decoded by the ASR module 102, and produces several variants of meaningful responses (questions or answers) and outputs this data as textual data to a text input 105 of the driver analyzer module 104.

The driver analyzer module 104 receives the textual output data from the NLP module 103 and receives voice data from the driver 101, and measures the time of response using a clock 113. An estimation of the quality of the textual responses of the driver (e.g., the ability to answer complex questions), time responses, and conclusions about the driver's alertfulness from the driver's voice patterns are generated and output to the conversational planner 107. In other words, the analysis by the driver analyzer module 104 is not only objective (i.e., did the driver respond verbally within a preset time), but also subjective (i.e., did the content of the response make sense). The module 104 is operative to generate complex responses that is used to determine the degree to which the driver is alert.

The conversational planner 107 instructs the language generator 108 as to the kind of response to produce. If the conversational planner finds that the driver continues to be in a perfect or acceptable condition for driving the car, the conversational planner instructs the language generator to continue the conversation in a "natural" manner, i.e., produce the response that is most pertinent to the semantic content of a previous driver's prompt. If, on the other hand, the conversational planner detects that the driver is becoming tired, then the language generator 108 is instructed to change the conversation (i.e., change the topic of conversation). For example, the language generator 108 can produce an unexpected joke ("The stock market fell 500 points! Oh, I am sorry, I was joking."), or play back real, but unexpected, news clips from the car media unit 130. For example, "there was an earthquake in Los Angeles." The language generator may also play temperament music. In order to produce a pertinent response, the conversational planner 107 stores information about the driver, such as the driver's tastes, hobbies, age, family, etc. in a driver profile module 121.

In accordance with the present invention, the conversational planner 107 measures a "surprise" element in each of the possible machine replies. This "surprise" measure is different from a probability value defining how likely a hypothesis sequence of words in a possible reply will occur. The "surprise" element in the hypothetical reply is measured as a conditional entropy measure of semantic content in the reply given the driver's prompt. The more unexpected a machine reply, the more additional information is contained in this reply, and the higher conditional entropy measure. The semantic criteria for "surprise" is acting in opposite direction than the probability measure whose objective is to specify the most likely sequence of words given the user prompt. These contradictionary goals can be considered as a minimum/maximum problem. A set of most probable hypothetical word paths is identified given a driver's prompt that satisfy grammatical, pragmatic and semantic constraints. Then, the least likely phrase is defined in this set from a semantic point of view (given the user prompt).

Other possible methods for naturally generated responses is described in W. Lehnert et al. "BORIS—An Experiment In-Depth Understanding of Narratives," Artificial Intelligence, 120(1) January 1983, pp. 15–62; and G. Ferguson et al., "The Design and Implementation of the TRAINS-96 System: A Prototype Mixed-initiative Planning Assistant" TRAINS Technical Note 96-5, The University of Rochester, Computer Science Department, October 1996, which is also incorporated herein by reference. Both publications are incorporated herein by reference.

There are interactions between an analyzer module and a conversation planner, such that if the system suspects that the driver's answers do not satisfy certain predefined criteria relating to the alertness of the driver, the system adjusts the questions to confirm this judgment.

If the conversational planner 107 receives information that suggests the driver is about to fall asleep, it activates an alarm system 111 that is programmable to produce a loud sound or produce some other physical impact on the driver (e.g., a stream of cold air). In determining whether the driver is about to fall asleep, the conversational planner considers other criteria such as: The quality of recognition and decoding by the ASR module 102, and the output of the NLP module 103. The conversational planner 107 may find that the ASR module 102 produced confusable decoding or semantically unclear statements.

For example, the planner 107 can ask the driver to repeat his reply ("Sorry, I did not understand you. Could you repeat what you just told me.") or try to change the subject conversation to a more narrower subject for which it can better identify the topic ("Oh, I just found that there is a PC EXPO on our way. Would you like to attend it?"). While the conversational planner guides the dialog with the driver it constantly analyzes the dynamic content of the car media 130 that is obtained from the intelligent text processor 120. The planner decides whether there is an interesting program from the car media 130 that is pertinent to the topic that is being discussed with the driver and that can be inserted into the dialog. From the driver profile 121, the conversational planner knows that the driver enjoys a certain music artist whose song is presently being played on the radio. In such a case, the conversational planner 107 may interrupt the conversation and state: "Listen, here is your favorite music artist!—let's hear him" and forward the radio program to a speaker 110 via the speech generator 109 that synthesizes text produced by the language generator 108, plays back recorded messages, or transfers the car media data to the speaker 110.

The language generator module 108 chooses the single textual phrase from several candidate phrases produced by the NLP module 103 on the basis of instructions from the conversational planner. Each candidate phrase from the NLP module satisfies different goals and criteria and the final phrase is chosen on the basis of the goal from the conversational planner.

The system also includes an external service provider adapter 122 for facilitating communications between the dialog car system and a remotely located external service provider 123. The external service provider 123 may be linked to the dialog car system through any one of various possible ways, such as cellular or other convenient wireless network systems.

The external service provider 123 is coupled through the adapter 122 to the car media module 130, driver analyzer module 104, the driver profile module 121 and conversational planner module 107. Coupled to the driver analyzer module 104, the external service provider receives alert signals if the module 104 finds that a driver is not responding properly to other alerting means (e.g., dialog, sounds and cold air produced by the system).

The external service provider is coupled to the car media 130, driver profile 121 and conversational planner module 107 in order to upgrade these modules with new data as it becomes available. The data may be collected from other services that are provided to many dialog systems installed in other automobiles. A monitoring system contained within the external service provider can evaluate the success of various sleep prevention systems and strategies in different cars. For example, if the external service provider determines that some conversational strategies are not as successful in preventing drivers from falling asleep as others, then data can be transmitted to each dialog system in other cars to update the appropriate modules such as the conversational planner 107 such that the less-effective strategies are rarely used or not used at all.

Conversely, if it is found that some strategies are more effective in preventing drivers from falling asleep (e.g., a particular type of conversation prompted an immediate laugh from many drivers) then data is transferred to other dialog systems such that those systems use the more effective strategies. In some instances, the actual content of the conversation will be transferred from the external service provider 123 to the conversational planner 107. For example, if some driver laughed where a random response was produced in a car that mentioned a joke, then that joke will be inserted in other car conversational planner modules 107 and used in those cars.

Figure 2:
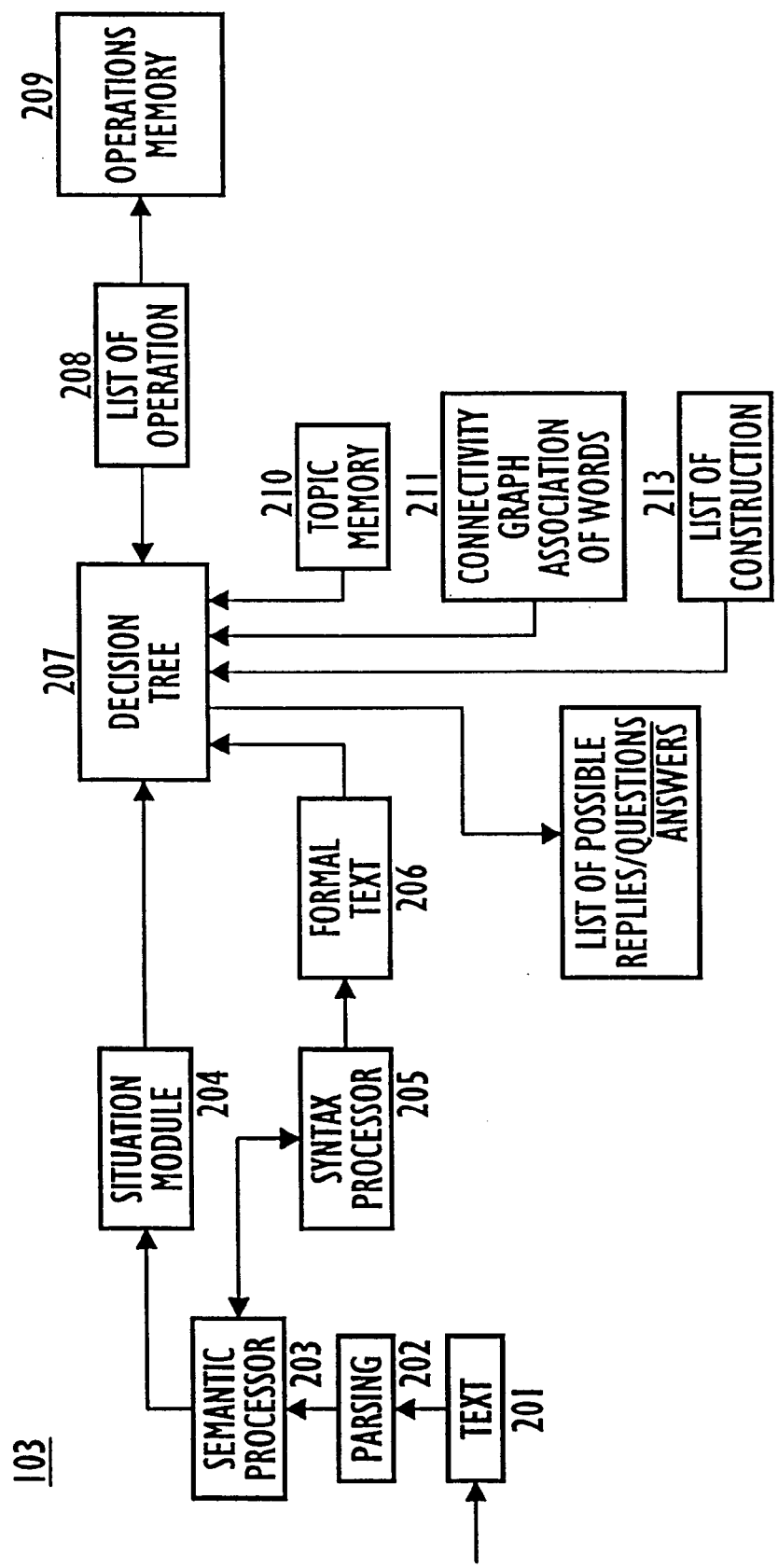
FIG. 2 illustrates an natural language processor module of the system of FIG. 1.

FIG. 2 illustrates the NLP module 103 of the system described above. The module 103 includes a parsing module 202 which receives the decoded output signal of text data 201 from the ASR module 102. The parsing module 202 attaches a parsing structure to the text as described in Jelinek et al., "Decision Tree Parsing Using a Hidden Derivation Model," Proceedings of the ARPA Workshop on human Language Technology, Princeton, N.J., March 1994, which is incorporated herein by reference. This module 202 parses data to produce grammatically correct and most likely associative responses. Such automatically generated responses generally have a well defined, sometimes humorous meaning that causes the driver to laugh. Those of ordinary skill in the art will recognize other techniques of parsing data sufficient to fulfill the purposes described herein.

A semantic processor 203 receives an output of the parsing module 202 and interprets the semantic content of each phrase input, using a list of words and associated semantic classes. The processor 203 interprets the syntactic position of the list of words and associated semantic classes in a sentence that is defined by a syntax processor 205. For example, the processor 203 interprets one word received from the syntax processor 205 as a VERB PHRASE and then finds a class of words associated with that given verb. The processor 203 similarly interprets other words which are a NOUN PHRASE or other grammatical PHRASES. A set of associated phrases provides semantic representation of the textual phrase. The semantic representation of the phrase is related to a situation by a situation module 204. The situation module defines a general category where the given semantic content occurs. For example, if the semantic content is relating to a question/answer such as: "I love to drink Coca-Cola?" "We need to stop and buy it"—the situation category can be expressed as "DRINKING". Similarly any phrases about love, meetings with girlfriends can be expressed as the situation "SEX". Phrases about children, wife, husband, mother or father can be expressed as the situation "FAMILY" or the content may be more in-depth, such as FAMILY-MEETING-YEAR-1996 in a given year (e.g., was 1996 a very significant year from the perspective of family life). These situations provide the most general context in which replies by the dialog system will follow the driver's prompts.

The situation categories are related to the list of topics stored in a topic memory 210 via a decision tree module 207. Each situation category is related to a list of topics and events that may happen under the situation category. For example, the "FAMILY" situation defines several topics as family dinners, father going with children to ZOO, etc. The "DRINKING" situation defines events such as someone is thirsty or people are in a bar ordering beer. These events under one situation category are not closely related. For example, two different events under the category "DRINKING" include someone is drinking coffee and someone is dying from thirst in a desert. The dialog system can jump from one event to another event in the same categorical situation. This gives the impression to the driver that his/her phrases and machine responses are situation related and produce humorous impression to the driver if the semantic relationship is weak. For example, the driver may ask the car system: "Do you want to drink coffee?" "The machine system can answer like "I am thirsty like I am in a desert." The car system has stereotypical phrases for a variety of situations stored in the memory 210.

The decision tree 207 operates with a set of questions (i.e., questions that are semantic, syntactic, pragmatics). The procedure of forming decision trees from questions and splitting a set of properties (semantic, pragmatics, syntactic, etc.) into subsets (i.e., forming questions) is based on a decision tree language module system, which is an extension of a technique described in L. Bahl et al. "A Tree-Based Statistical Language Model for Natural Language Speech Recognition," IEEE Transactions on Acoustics, Speech and Signal Processing Vol. 37, No. 7, July 1989, which is incorporated herein by reference. The basic difference is that questions in this work were "structural"—like about word relative positions in a sentence. But, according to the present invention, the decision tree is a mixture of all properties of different nature—semantic, grammar, pragmatics and questions may integrate semantic and syntactic information.

Here, the decision tree uses a set of questions concerning different factors such as the driver's interests (hobby, profession, age, etc.) his/her physical conditions, conditions outside of the car (night or day, winter or summer as examples), traffic conditions, and so on. Other sets of questions are related to the driver's replies (for example, "Is the first word a name? Is the second word an action? How long is his phrase? Some questions concern parsing of a phrase, pragmatics and semantics, while some questions are just splits of sets of some properties related to a driver such as answers, conditions, history, etc.)" These questions form a decision tree, which is related to a set of actions and interactions with all modules. These actions can be: ask other question, send a warning signal, play music, activate a radio set, tell news from a radio, produce a joke or other meaningful replies.

The formal text module 206 produces data which is in response to the output by the syntax processor 205 and which consist of formal representation of a sentence (representing logical structure of the sentence and a canonical order e.g., ADJECTIVE NOUN, VERB, etc.) and formal actions between WORDS (e.g., VERB modifies NOUN). These syntactic formal representation is related to the formal semantic representation of each word (e.g., NOUN—WATER, VERB—DRINK and action DRINK(WATER), i.e., a verb acts on a noun. Methods of generating a formal representation of phrases are known in the art. A few methods are described in Gerhard Gazdar and Chris Mellish, "Natural Language Processing in POP-11," and Addison-Wiley Publishing Company, New York, 1989, both of which are incorporated herein by reference.

A list of operation module 208 contains a list of operations that can be performed with formal sentences from the formal text module 206. The operations are stored in an operations memory 209. The operations include, for example, substitution (e.g., WATER can be replaced by COCA-COLA), recursion (e.g., the phrase HE SAID THAT can be extended as HE SAID THAT HE SAID etc.), and concatenation, (e.g., two phrases can be connected with AND). There are also a set of formal operations that convert questions to a non-question phrase (e.g., "Does he like Coca-Cola?"—"He likes Coca-Cola."). This list of operations is applied in random order by the decision tree 207 in accordance with predefined decision tree criteria. A connectivity graph module 211 includes words connected with paths if two words are met in the same sentence or have an association of words. See, W. Zadrozny and K. Jensen, "Semantics of Paragraphs," Computational Linguistics, 17(2): 171–210, 1991.

The associative word graphs are used to associate a set of words given input phrase from the text data 201 after it is formally represented by the decision tree 207. These associated sets of words give rise to a set of associated phrases after formal semantic and syntactic rules are applied to select correct phrases by the list of operation module 208. There is also a list of constructions 213 that represents a full set of possible constructions that involve time or place (e.g., at 5:00, in restaurant etc.) as described in A. E. Goldberg, "Constructions: A Construction Grammar Approach to Argument Structure," The University of Chicago Press, Chicago, Ill., 1995 (which is incorporated herein by reference). All of this gives rise to a set of possible replies 212 of questions and answers given the driver's input when prompted.

Figure 3:
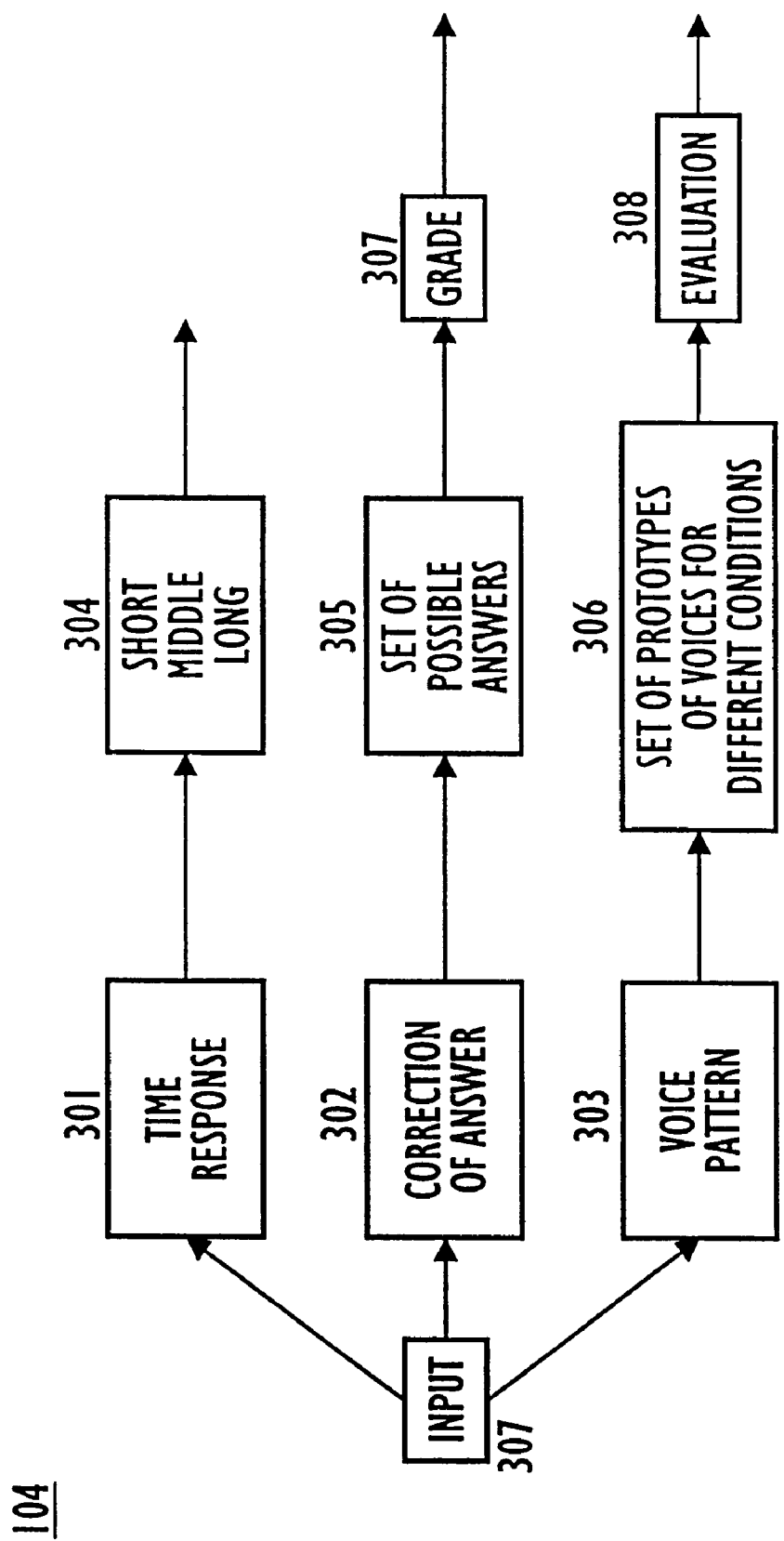
FIG. 3 illustrates a driver analyzer module of the system of FIG. 1.

FIG. 3 describes the driver analyzer module 104 as follows. An input data stream 307 (including voice and text data that is time stamped when the driver received a voice prompt from a car system and when he answered) is input to a time response module 301, a correctness of answer module 302, and a voice pattern module 303. The difference in the time (time response) is classified as "short," "middle," or "long" by a time evaluator module 304. The answers (textual) are matched with prototypes of possible answers by module 305 and evaluated by a grading module 307 (e.g., very good, good, bad). Voice patterns are matched with a set of voice patterns in a voice pattern module 306, which characterizes various characteristics of voice—pitch, breathing, vagueness, loudness, etc. The sets of prototypes were created from the driver under various known conditions (before going to sleep, in the morning, etc.). In an evaluator module 308, the evaluation is done on the kind of prototypes that best matches the driver's voice condition.

Figure 4:
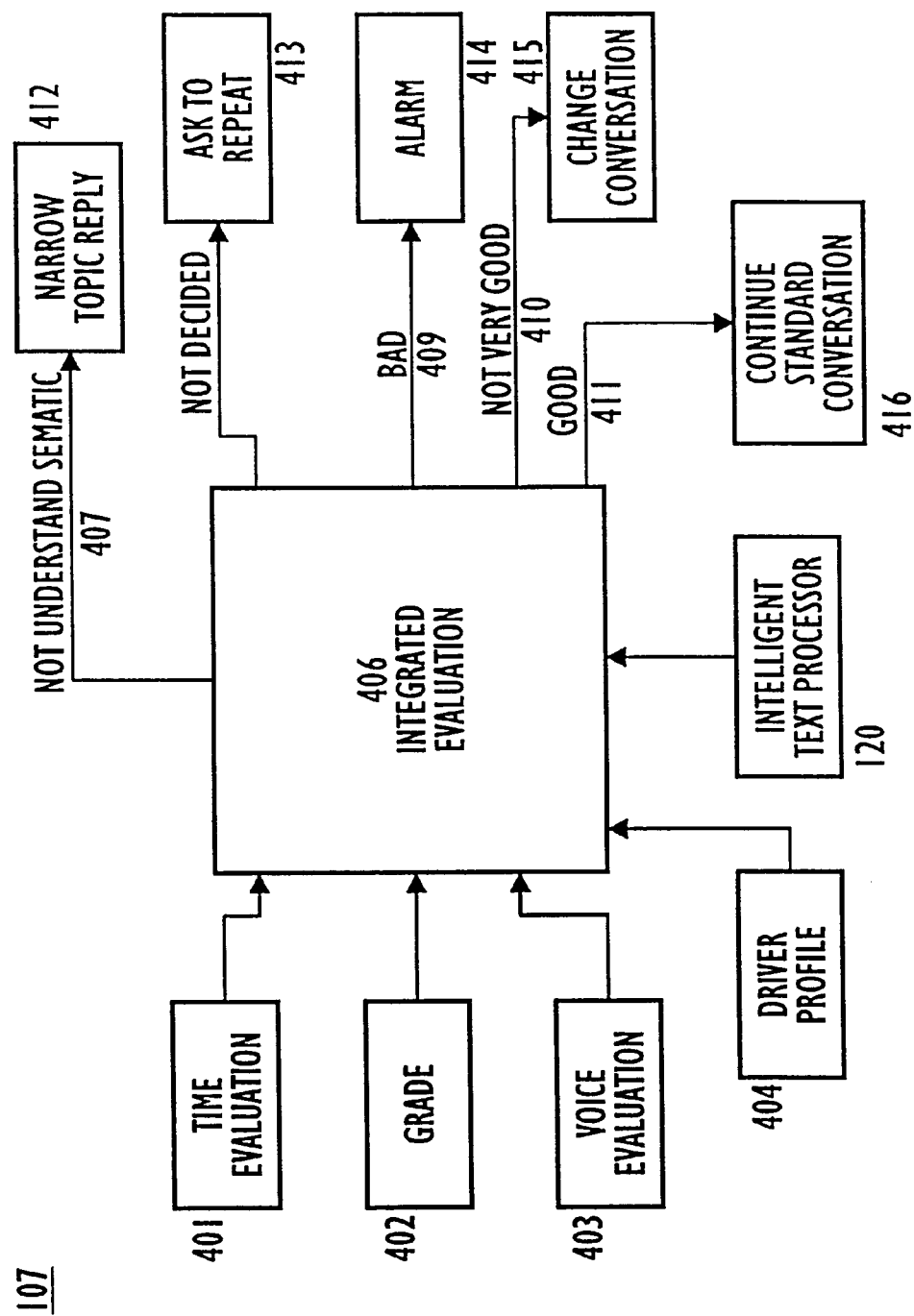
FIG. 4 illustrates a conversational planner module of the system of FIG. 1.

FIG. 4 illustrates the conversational planner module 107. A time evaluation module 401, grading module 402, a voice evaluation module 403 are entered into an integrated evaluation module 406. The time evaluation module 401, grading module 402, and voice evaluation module 403 are similar to the modules 304, 307 and 308, respectively, described above and shown in FIG. 3. The evaluation can be done as weighted sum of evaluations with each criteria.

On the basis of the evaluation different responses are possible. If the module 406 determines that the system did not understand the semantics of the driver's answer it can ask specific questions by outputting a signal on line 407 to the module 412. For example, the module can use the driver profile 404 to ask a question about him that should produce a narrow topic of reply (e.g., "How long have you been married?"). If the module 406 does not understand the answer it can ask the driver via line 408 and module 413 to repeat the answer ("Sorry, please repeat the answer." or "I did not hear you."). If the evaluation module 406 detects that the driver is falling asleep it activates an alarm 414 via signal path 409. If the driver's condition is determined to be neither good nor bad, the evaluator 406 outputs a middle signal on line 410 to the change conversation module 415, which then changes the conversation topic. The module 415 uses the information from the intelligent textual processor 120 if it can help change the subject (e.g., tell a breaking news article). If the driver's condition is good then the evaluator 406 outputs a good signal on line 411 to the continue standard conversation module 416 so that the dialog continues in a natural manner.

There has thus been shown and described a sleep prevention dialog based car system which fulfills all the objects and advantages sought therefor. Many changes, modifications, variations and other uses and applications of the subject invention will, however, become apparent to those skilled in the art after considering the specification and the accompanying drawings which disclose preferred embodiments thereof. For example, the dialog system can be portable or a handheld device, and be easily adapted to other applications. The dialog system will be applicable to other situations where the individual(s) must stay alert, such as security guards, operators at nuclear plants or other types of plants or manufacturing facilities, pilots of airplanes, trains, ships and so on. All such changes, modifications, variations and other uses and applications which do not depart from the spirit and scope of the invention are deemed to be covered by the invention which is limited only by the claims which follow.

What is claimed is:

1. A dialog car system comprising:
   a speech recognition circuit, operative to receive words an sounds uttered by a drive of a vehicle, and to produce decoded voice signals corresponding to said words and sounds;
   a natural language processor coupled to receive said decoded voice signals output by speech recognition circuit, and being operative to process and produce responses based on said decoded voice signals;
   a speech generator, responsive to an output derived from said natural language processor, for generating speech for the driver to hear so as to carry on a dialog with the driver;
   an analyzer, coupled to said natural language processor and said speech recognition circuit, for analyzing the words and sounds uttered by the drive and to determine whether the drive is alert or about to fall asleep; and
   a conversational planner, coupled to an output of said driver analyzer for planning the type and content of speech to generate by said speech generator, wherein said conversational planner comprises means for receiving indications of conditions of the driver, means for continuing the dialog when said conditions of the driver are within an acceptable level, and means for changing the dialog when at least one of said conditions of the driver is outside an acceptable level.

2. The dialog car system as defined by claim 1, further comprising:
   an intelligent text processor, coupled to an input of said conversational planner, for producing various types of dialog to be considered by said conversational planner to be included in the dialog with the driver; and
   a car media, coupled to said intelligent text processor, being operative to produce audio programming information based on a plurality of sources.

3. The dialog car system as defined by claim 2, wherein said car media comprises means for receiving programming information from a plurality of sources; said system further comprising means for recognizing a certain word or series of words in said programming information, to allow predefined audio programming to be selected and transferred to said conversational planner.

4. The dialog car system as defined by claim 3, wherein said plurality of sources includes one or more of audio tapes, audio books, CD player units, DVD player units, telephonic communications, radio, sites on the internet, and remote audio input.

5. The dialog car system as defined by claim 1, further comprising an alarm, coupled to an output of said conversational planner, and being activated to produce an alarm when said conversational planner detects that the driver is about to fall asleep, wherein said audio alarm includes at least one of the following: an audio alarm, a visual alarm, and physically impacting the driver.

6. The dialog car system as defined by claim 1, further comprising a driver profile module for storing information particular to the driver, wherein said conversational planner is responsive to said information stored in said driver profile module for planning the type and content of dialog with the driver.

7. The dialog car system as defined by claim 1, further comprising a language constrain module coupled between said speech recognition circuit and speech generator, and wherein said language constrain module dynamically constrains said speech recognition circuit to produce said decoded voice signals restricted to predetermined topics of conversation.

8. The dialog car system as defined by claim 1, wherein said natural language processor comprises:
   a parsing module which receives said decoded voice signals including text data from said speech recognition circuit, for parsing structure of said text data to produce structural descriptions of said text;
   a semantic processor, coupled to an output of said parsing module, for interpreting semantic content of each phrase output by said parsing module;
   a situation module, coupled to an output of said semantic processor, for relating an output of said semantic processor to one of a plurality of situations stored in a first memory module;
   a formal text module responsive to an output of said semantic processor for generating a formal representation of phrases, including logical structures and correlations between verbs and nouns;
   a second memory module for storing a list of operations that can be performed with formal sentences from said formal text module;
   a third memory module for storing a list of possible replies to decoded voice signals received from the driver;
   a connectivity graph module for connecting words with paths if two words are met in the same sentence or have an association of words; and
   a decision tree coupled to said situation module; formal text module; second memory module, third memory module, and connectivity graph module, for processing and producing meaningful responses, and outputting said meaningful responses to said conversational planner.

9. The dialog car system as defined by claim 1, wherein said driver analyzer comprises:
   input means for receiving an input data stream, including voice and text data;
   a time evaluator, coupled to said input means, for time stamping said voice and text data corresponding to when the driver receives a voice prompt and when the driver answers, and for evaluating the length of time to respond to an inquiry;
   an answer evaluator, coupled to said input means, for evaluating said input data stream, determining whether said input data stream matches a predetermined set of possible answers, and grading said input data stream on a scale; and
   a voice pattern evaluator, coupled to said input means, for matching said input data stream with a predetermined set of voice patterns to detect one or more characteristics of said input data stream.

10. The dialog car system as defined by claim 1, wherein said conversational planner comprises: an integrated evaluator, responsive to outputs of said driver analyzer, for classifying responses of the driver into different categories depending on predetermined characteristics of the response, and determining a state of condition of the driver.

11. The dialog car system as defined by claim 10, wherein said conversational planner comprises means for determining whether to continue dialog in a normal manner, means for determining whether a response from the driver was at least one of good, not very good, bad, or not understood.

12. A dialog car system comprising:
- a speech recognition circuit, operative to receive words and sounds uttered by a driver of a vehicle, and to produce decoded voice signals corresponding to said words and sounds;
- a natural language processor, coupled to receive said decoded voice signals output by said speech recognition circuit, and being operative to process and produce responses based on said decoded voice signals;
- a driver analyzer, coupled to said natural language processor and said speech recognition circuit, for analyzing said decoded voice signals and to determine whether the driver is alert or about to fall asleep;
- a driver profile module for storing information particular to the driver;
- a car media operative to produce programming information from a plurality of sources;
- an intelligent text processor, coupled to an output of said car media, for producing various types of dialog to be considered by a conversational planner to be included in the dialog with the driver; and
- said conversational planner, responsive to said information stored in said driver profile module and coupled to an output of said driver analyzer and an output of said intelligent text processor, for planning the type and content of speech based on input received from said driver analyzer and intelligent text processor;
- a speech generator, responsive to an output derived from said conversational planner, for generating speech for the driver to hear to carry on a dialog with the driver; and
- an external service provider, coupled to said car media, driver profile and conversational planner in order to upgrade said car media, driver profile and conversational planner with new data, including type and content of programming information.

13. The dialog car system as defined by claim 12, further comprising an adapter for coupling said external service provider to said car media, driver analyzer, driver profile and conversational planner module.

14. The dialog car system as defined by claim 12, further comprising an alarm, coupled to an output of said conversational planner, and being activated to produce an alarm when said conversational planner detects that the driver is about to fall asleep, wherein said alarm includes at least one of the following: an audio alarm, a visual alarm, and physically impacting the driver.

15. The dialog car system as defined by claim 13, wherein said external service provider receives alert signals from said analyzer if it is determined that the driver is not responding properly to activation of said alarm.

16. The dialog car system as defined in claim 15, wherein said external service provider evaluates the success rates of various types and contents of programming information, and updates the dialog car system to implement programming information that is successful in preventing a driver from falling asleep.

* * * * *